United States Patent
Eskesen

(10) Patent No.: US 11,697,628 B2
(45) Date of Patent: Jul. 11, 2023

(54) METHOD FOR THE PREPARATION OF METHANOL

(71) Applicant: Topsøe A/S, Kgs. Lyngby (DK)

(72) Inventor: Søren Grønborg Eskesen, Espergærde (DK)

(73) Assignee: Topsoe A/S, Kgs. Lyngby (DK)

( * ) Notice: Subject to any disclaimer, the term of this patent is extended or adjusted under 35 U.S.C. 154(b) by 0 days.

(21) Appl. No.: 17/774,785

(22) PCT Filed: Nov. 30, 2020

(86) PCT No.: PCT/EP2020/083819
§ 371 (c)(1),
(2) Date: May 5, 2022

(87) PCT Pub. No.: WO2021/110565
PCT Pub. Date: Jun. 10, 2021

(65) Prior Publication Data
US 2022/0388934 A1    Dec. 8, 2022

(30) Foreign Application Priority Data
Dec. 3, 2019 (DK) .......................... PA 2019 01417

(51) Int. Cl.
C07C 29/151    (2006.01)
C07C 29/92     (2006.01)
C07C 31/04     (2006.01)

(52) U.S. Cl.
CPC .......... *C07C 29/1516* (2013.01); *C07C 29/92* (2013.01); *C07C 31/04* (2013.01)

(58) Field of Classification Search
CPC ...... C07C 29/1516; C07C 29/92; C07C 31/04
See application file for complete search history.

(56) References Cited

U.S. PATENT DOCUMENTS

| 3,950,369 A | 4/1976 | Gent et al. |
| 5,523,326 A * | 6/1996 | Dandekar .............. C12C 11/02 518/706 |
| 2015/0251983 A1 | 9/2015 | Panza et al. |
| 2019/0047931 A1 | 2/2019 | Balthasar et al. |
| 2019/0185396 A1 | 6/2019 | Schulz et al. |

OTHER PUBLICATIONS

P.J. Dahl et al., "Proven ATR Technology for Methanol Plants." Nitrogen + Syngas, No. 331, pp. 36-41, 2014.

* cited by examiner

*Primary Examiner* — Yate' K Cutliff
(74) *Attorney, Agent, or Firm* — Blank Rome LLP

(57) ABSTRACT

A method for the preparation of methanol by conversion of a mixture of fresh methanol synthesis gas and unconverted methanol synthesis separated from produced methanol in a low pressure separator and recycled and admixed to the fresh synthesis gas upstream the suction side of a make-up gas compressor.

3 Claims, No Drawings

METHOD FOR THE PREPARATION OF METHANOL

The present invention relates to the preparation of methanol by conversion of synthesis gas into methanol. In particular, the invention is a method for the preparation of methanol by conversion of a mixture of fresh methanol synthesis gas and unconverted methanol synthesis gas separated from produced methanol in a low pressure separator and recycled and admixed to the fresh synthesis gas upstream the suction side of a make-up gas compressor.

By the method of the invention valuable unconverted synthesis gas is avoided, which in the known methods for the preparation typically is purged to the atmosphere or used as fuel.

Methanol synthesis gas is any gas composition comprising hydrogen and carbon dioxide and/or carbon monoxide. The methanol synthesis gas is typically described in terms of its Module, $M=(H_2-CO_2)/(CO+CO_2)$. The syngas is in balance for the methanol reaction when the module is equal to 2.

Heterogeneous methanol synthesis is in today's practice carried out by reacting carbon oxides with hydrogen in the presence of copper-based catalysts according to the following equations:

$$3H_2+CO_2=CH_3OH+H_2O \quad (1)$$

$$2H_2+CO=CH_3OH \quad (2)$$

The methanol synthesis catalyst also catalyses the Water Gas Shift (WGS) reaction, $$CO+H_2O=CO_2+H_2 \quad (3)$$

and the Reverse Water Gas Shift (RWGS) reaction, $$CO_2+H_2=CO+H_2O \quad (4)$$

The synthesis gas used in methanol synthesis can be derived from natural gas either by steam-methane reforming, optionally followed by an oxygen-fired secondary reformer, or by autothermal reforming alone.

To obtain maximum use of the produced synthesis gas, a recycle of a part of unconverted gas contained in the methanol reactor effluent is necessary. Before recycling, the methanol reactor effluent is cooled and separated from the liquid methanol product in a high pressure separator.

Further separation of unconverted synthesis gas from produced methanol is achieved in a low pressure separator.

The standard solution is to pass the gas from the low pressure separator to a purge gas line thereby sending it out of the synthesis section. The pressure in the low pressure separator is typically about 4 bar g.

Usually, it does not pay off to recycle the unconverted synthesis gas from the low pressure separator because the pressure of the separated gas is much lower than of the fresh synthesis gas upstream the make-up compressor, being around 28 bar g.

If the pressure of the gas to the make-up gas compressor is low, i.e. lower than the pressure in the low pressure separator, the gas from the low pressure separator can be recycled to the suction side of the make-up gas compressor and added to the existing make-up gas.

Accordingly, the invention is a method for the preparation of methanol from a synthesis gas comprising hydrogen and carbon dioxide comprising the steps of (a) mixing fresh methanol synthesis gas and unconverted methanol synthesis gas withdrawn from a downstream low pressure separator and passing the synthesis gas mixture to suction side of a make-up gas compressor and pressurizing the synthesis gas mixture;

(b) introducing and converting the pressurized synthesis gas mixture into one or more methanol reaction stages in presence of a methanol catalyst;

(c) withdrawing from step (b) a reacted effluent comprising methanol and the unconverted synthesis gas;

(d) cooling the reacted effluent below dew point of methanol;

(e) separating a part of the methanol in a high pressure separator and a part of the unconverted synthesis gas and recycling the part of the unconverted gas via a recycle compressor to the discharge side of the make-up gas compressor;

(f) separating a further part of the methanol from a further part of the unconverted synthesis gas in the low pressure separator;

(g) recycling at least a part of the unconverted synthesis gas from step (f) to step (a) upstream the suction side of the make-up gas compressor, wherein pressure of the fresh synthesis gas in step (a) is lower than the pressure of the unconverted synthesis gas withdrawn from the low pressure separator in step (f).

In an embodiment of the invention, the synthesis gas mixture further comprises carbon monoxide.

In further an embodiment of the invention, a part of the unconverted synthesis gas separated in the high pressure separator is passed to a purge gas scrubber and liquid from the purge gas scrubber is passed to the low pressure separator.

The advantages and effects of the invention are lowering of the module M of the synthesis gas passed into the methanol synthesis stage and making the gas more optimal for methanol production;

saving produced methanol that would otherwise be lost when purging the gas separated in the low pressure separator.

This can be utilized in several ways, namely:

Feedstock flow saving: Saving on feedstock while maintaining power input and production output;

Power saving: Saving on compression power input while maintaining feedstock flow and production output.

Production increase: Obtaining increased production output while maintaining feedstock flow and power input.

The invention claimed is:

1. Method for the preparation of methanol from a synthesis gas comprising hydrogen and carbon dioxide comprising the steps of (a) mixing fresh methanol synthesis gas and unconverted methanol synthesis gas withdrawn from a low pressure separator and passing the synthesis gas mixture to suction side of a make-up gas compressor and pressurizing the synthesis gas mixture;

(b) introducing and converting the pressurized synthesis gas mixture into one or more methanol reaction stages in presence of a methanol catalyst;

(c) withdrawing from step (b) a reacted effluent comprising methanol and the unconverted synthesis gas;

(d) cooling the reacted effluent below dew point of methanol;

(e) separating a part of the methanol in a high pressure separator and a part of the unconverted synthesis gas and recycling the part of the unconverted gas via a recycle compressor to the discharge side of the make-up gas compressor;

(f) separating a further part of the methanol from a further part of the unconverted synthesis gas in the low pressure separator;

(g) recycling at least a part of the unconverted synthesis gas from step (f) to step (a) upstream the suction side of the make-up gas compressor, wherein pressure of the fresh synthesis gas in step (a) is lower than the pressure of the unconverted synthesis gas withdrawn from the low pressure separator in step (f).

2. Method of claim 1, wherein the synthesis gas mixture further comprises carbon monoxide.

3. Method of claim 1, wherein a part of the unconverted synthesis gas separated in the high pressure separator is passed to a purge gas scrubber and liquid from the purge gas scrubber is passed to the low pressure separator.

* * * * *